(12) United States Patent
Levine et al.

(10) Patent No.: US 12,070,479 B1
(45) Date of Patent: Aug. 27, 2024

(54) DECARBOXYLATED CANNABIS COMPOSITIONS AND METHODS OF MAKING THE SAME

(71) Applicant: PT Worldwide, Studio City, CA (US)

(72) Inventors: Alexander John Levine, Studio City, CA (US); David Spiegel, Hamden, CT (US)

(73) Assignee: PT WORLDWIDE, Studio City, CA (US)

( * ) Notice: Subject to any disclaimer, the term of this patent is extended or adjusted under 35 U.S.C. 154(b) by 0 days.

(21) Appl. No.: 17/659,736

(22) Filed: Apr. 19, 2022

Related U.S. Application Data

(60) Provisional application No. 63/176,560, filed on Apr. 19, 2021.

(51) Int. Cl.
| | | |
|---|---|---|
| *A61K 31/352* | (2006.01) | |
| *A61K 31/05* | (2006.01) | |
| *A61K 36/185* | (2006.01) | |
| *B01D 5/00* | (2006.01) | |
| *B01J 6/00* | (2006.01) | |

(52) U.S. Cl.
CPC ............ *A61K 36/185* (2013.01); *A61K 31/05* (2013.01); *A61K 31/352* (2013.01); *B01D 5/006* (2013.01); *B01J 6/008* (2013.01)

(58) Field of Classification Search
CPC .................................................. A61K 31/352
See application file for complete search history.

(56) References Cited

U.S. PATENT DOCUMENTS

| | | |
|---|---|---|
| 10,517,911 B2 | 12/2019 | Gharib et al. |
| 10,676,453 B1 | 6/2020 | Hoskins |
| 10,941,131 B1 | 3/2021 | Grondin et al. |
| 2020/0299216 A1 | 9/2020 | Navickas |
| 2021/0230645 A1 * | 7/2021 | Ortiz ......................... A01H 6/28 |
| 2022/0324780 A1 * | 10/2022 | Levine ................. A61K 31/352 |

FOREIGN PATENT DOCUMENTS

| | | | |
|---|---|---|---|
| CA | 2503310 A1 | 10/2005 | |
| WO | WO-2020123522 A1 * | 6/2020 | ........... A23L 33/105 |

OTHER PUBLICATIONS

Dussy et al., "Isolation of Delta9-THCA-A from hemp and analytical aspects concerning the determination of Delta9-THC in cannabis products," Forensic Science International, 149 (2005), pp. 3-10.
Moreno et al., "Cannabinoid Decarboxylation: A Comparative Kinestic Study," Industrial and Engineering Chemistry Research, ACS Publications, Oct. 2020, pages A-I.
Wang et al., "Decarboxylation study of acidic cannabinoids: a novel approach using ultra-high-performance supercritical fluid chromatography/photodiode array-mass spectrometry," Cannabis and Cannabinoid Research, vol. 1.1, 2016, pp. 262-271.

* cited by examiner

*Primary Examiner* — John S Kenyon
(74) *Attorney, Agent, or Firm* — ArentFox Schiff LLP

(57) ABSTRACT

Decarboxylated *cannabis* compositions and methods of making and using the same are provided. The methods produce a decarboxylated product that has more terpenes and cannabidiol preserved and less oxidation of tetrahydrocannabinol to cannabinol, compared to a decarboxylated product made by a traditional decarboxylation process.

20 Claims, No Drawings

DECARBOXYLATED CANNABIS COMPOSITIONS AND METHODS OF MAKING THE SAME

CROSS-REFERENCE TO RELATED APPLICATIONS

This application claims priority from U.S. Provisional Patent Application No. 63/176,560, filed Apr. 19, 2021, the contents of which are incorporated herein by reference.

FIELD OF THE DISCLOSURE

The present disclosure relates generally to compositions comprising decarboxylated *cannabis*, and methods of making the same.

SUMMARY OF THE DISCLOSURE

The present disclosure generally relates to a method for preparing a decarboxylated *cannabis* composition, comprising: (a) adding *cannabis* material to a reaction chamber, (b) treating the reaction chamber with inert gas, (c) sealing the reaction chamber, (d) initiating a decarboxylation reaction of the *cannabis* material at about 70° C. to about 150° C., for about 1 to about 10 hours in the sealed reaction chamber, (e) condensing within the sealed reaction chamber at about 0° C. to about 20° C., (f) retaining a decarboxylated *cannabis* composition within the sealed reaction chamber, (g) optionally, storing the sealed reaction chamber comprising the decarboxylated *cannabis* composition at a temperature of about −20° C. to about −40° C., and (h) unsealing the sealed reaction chamber to form an unsealed reaction chamber comprising the decarboxylated *cannabis* composition, wherein no or substantially no solvent is added to the reaction chamber, and wherein no by-products are removed from the reaction chamber prior to the unsealing of the sealed reaction chamber. The present disclosure also generally relates to a decarboxylated *cannabis* composition made by this method.

The present disclosure also generally relates to a vaporizer or vaporizer cartridge comprising a comprising a decarboxylated *cannabis* composition comprising: about 25% to about 90% (wt. %) of tetrahydrocannabinol (THC), up to about 10% (wt. %) of terpenes, and no or substantially no tetrahydrocannabinolic acid (THCA), cannabidiolic acid (CBDA), or cannabigerolic acid (CBGA), and no or substantially no additives.

The present disclosure also generally relates to a vaporizable decarboxylated *cannabis* composition comprising: about 25% to about 90% (wt. %) of tetrahydrocannabinol (THC), up to about 10% (wt. %) of terpenes, no or substantially no tetrahydrocannabinolic acid (THCA), cannabidiolic acid (CBDA), or cannabigerolic acid (CBGA), and no or substantially no additives.

The present disclosure also generally relates to a composition comprising decarboxylated rosin, wherein the composition comprises substantially no additives and substantially no tetrahydrocannabinolic acid (THCA), cannabidiolic acid (CBDA), or cannabigerolic acid (CBGA).

The present disclosure also generally relates to composition comprising decarboxylated rosin, wherein the composition comprises no additives and no tetrahydrocannabinolic acid (THCA), cannabidiolic acid (CBDA), or cannabigerolic acid (CBGA). In other aspects, the decarboxylated rosin has more terpenes and cannabidiol preserved, and less oxidation of tetrahydrocannabinol to cannabinol, compared to a decarboxylated rosin produced by a traditional decarboxylation process (e.g., vacuum ovens, open vessels in traditional ovens).

DETAILED DESCRIPTION

The present disclosure generally relates to compositions comprising *cannabis* compounds. The term "*cannabis* compound" refers to compounds that are found in *cannabis*. *Cannabis* refers to a genus of plants in the family Cannabaceae. Species of *cannabis* include, but are not limited to: *Cannabis sativa*, *Cannabis indica*, and *Cannabis ruderalis*. Different strains and hybrids of these *cannabis* species exist. Examples of *cannabis* compounds include, but are not limited to, cannabinoids and terpenes.

*Cannabis* compounds may be administered to subjects for a variety of reasons, such as the treatment, prevention, and/or amelioration or reduction of symptoms relating to physiological conditions including, but not limited to, pain, inflammation, nausea, vomiting, loss of appetite, weight loss, nerve-related disorders, mood disorders, sleep disorders, musculoskeletal disorders, and glaucoma.

The present disclosure relates to decarboxylated *cannabis* compositions, and methods of decarboxylating *cannabis* compounds. Decarboxylation refers to a chemical reaction wherein a carboxyl group is removed from a compound and replaced with a hydrogen atom. During a decarboxylation reaction, one or more by-products may be formed and/or released. Examples of by-products include but are not limited to carbon dioxide ($CO_2$).

Decarboxylated compounds refer to compounds wherein a carboxyl group has been removed via a decarboxylation process. Some compounds found in *cannabis* contain carboxyl groups that can be removed by a decarboxylation process. Some *cannabis* compounds are converted to active ingredients, or compounds having pharmacological activity or a biological effect, when they are decarboxylated. For example, after decarboxylation, tetrahydrocannabinolic acid (THCA) is converted to tetrahydrocannabinol (THC), cannabidiolic acid (CBDA) is converted to cannabidiol (CBD), and cannabigerolic acid (CBGA) is converted to cannabigerol (CBG). These decarboxylated *cannabis* compounds (THC, CBD, and CBG) are typically desired for their pharmacological activity and biological effects and are preferred over their acid precursors. The term "decarboxylated *cannabis* composition" refers to a composition comprising one or more decarboxylated *cannabis* compounds.

The present disclosure generally relates to a method for preparing a decarboxylated *cannabis* composition, comprising: (a) adding *cannabis* material to a reaction chamber, (b) treating the reaction chamber with inert gas, (c) sealing the reaction chamber, (d) initiating a decarboxylation reaction of the *cannabis* material at about 70° C. to about 150° C., for about 1 to about 10 hours in the sealed reaction chamber, (e) condensing within the sealed reaction chamber at about 0° C. to about 20° C., (f) retaining a decarboxylated *cannabis* composition within the sealed reaction chamber, (g) optionally, storing the sealed reaction chamber comprising the decarboxylated *cannabis* composition at a temperature of about −20° C. to about −40° C., and (h) unsealing the sealed reaction chamber to form an unsealed reaction chamber comprising the decarboxylated *cannabis* composition, wherein no or substantially no solvent is added to the reaction chamber, and wherein no by-products are removed from the reaction chamber prior to the unsealing of the sealed reaction chamber.

In some aspects, the method of preparing a decarboxylated *cannabis* composition comprises a step of adding *cannabis* material to a reaction chamber. The term "*cannabis* material" refers to material comprising *cannabis* compounds. In some aspects, the *cannabis* material comprises *cannabis* extracts, *cannabis* concentrates, dried or live *cannabis* plant matter, or mixtures thereof. The mixtures thereof may refer to mixtures of one of more types of *cannabis* material, mixtures of one or more *cannabis* extracts or one or more *cannabis* concentrates, or a combination thereof. In some aspects, a *cannabis* extract refers to a preparation containing one or more *cannabis* compounds, obtained by an extraction process involving a *cannabis* plant material. In some aspects, *cannabis* extract is obtained by a solvent-based extraction process, using solvents including, but not limited to, ethanol, isopropyl alcohol, n-propyl alcohol, methanol, butane, isobutane, propane, and carbon dioxide. Examples of *cannabis* extracts include, but are not limited to butane hash oil (BHO), carbon dioxide oil, and resin.

In some aspects, a *cannabis* concentrate refers to a preparation containing one or more *cannabis* compounds, obtained by heat and/or pressure processing methods or other mechanical means. In some aspects, *cannabis* concentrate is obtained without the use of a solvent (i.e., a solventless process). Examples of *cannabis* concentrates include, but are not limited to rosin, hash, and kief. In some embodiments, the *cannabis* material comprises rosin, which is a *cannabis* concentrate obtained by heat and pressure in a solventless process.

In some aspects, the *cannabis* concentrate or *cannabis* extract are produced using freshly harvested plant matter and are referred to as "live" *cannabis* concentrates or "live" *cannabis* extracts. In some aspects, the *cannabis* concentrate or *cannabis* extract are produced using plant matter has been frozen after harvesting. In some aspects, the freezing process occurs immediately or soon after harvesting. In some aspects, the plant matter is flash frozen.

In some aspects, the *cannabis* material refers to dried or live *cannabis* plant matter. Dried *cannabis* plant material may refer to plant matter that is subjected to drying methods to achieve a desired water content level. Live *cannabis* plant material may refer to plant matter that is fresh and uncured and not subject to any processing. Plant matter includes one or more parts of the *cannabis* plant, including, but not limited to, the flower, bud, node, stem or stalk, leaves, seeds, and roots.

In some aspects, the process comprises a step of adding *cannabis* material to a reaction chamber. The reaction chamber may refer to any vessel in which a decarboxylation reaction can occur. In some aspects, the reaction chamber is a vessel is comprised of a material such as glass, porcelain, or steel, or any material that does not react with its contents. In some aspects, the reaction chamber is a vessel that is comprised of a heat-proof material. In some embodiments, the reaction chamber comprises a borosilicate glass vessel. In some aspects, the reaction chamber comprises a vessel that does not include a filter or a coil. In some aspects, the reaction chamber comprises a vessel that does not comprise a filter for the removal of by-products from the decarboxylation process. In some aspects, prior to the addition of *cannabis* material, the reaction chamber is cleaned and dried. In some aspects, the reaction chamber is cleaned with ethanol, including pure ethanol, or another substance that leaves no or minimal residue and/or no or minimal amount of reactive compounds. The reaction chamber is then optionally subsequently rinsed with distilled water and optionally subsequently dried, for example, with an air dryer or using an inert drying towel. In some aspects, the reaction chamber is cleaned with a substance that does not comprise isopropyl alcohol or reactive solvent. In some aspects, the *cannabis* material is added in an amount sufficient to fill the vessel but to allow room for the formation of by-products.

In some aspects, the process comprises a step of treating the reaction chamber with inert gas. In some aspects, this step occurs prior to the decarboxylation reaction. In some aspects, inert gas is introduced in a manner sufficient to purge or flush the reaction chamber to create an inert atmosphere. In some aspects, the inert gas comprises nitrogen, argon, helium, neon, and xenon. In some embodiments, the inert gas comprises nitrogen. The treatment of the reaction chamber may be conducted by various means, including but not limited to the use of a gas nozzle associated with a gas tank, or systems comprising gas piping, valves, or some suitable equipment. In some embodiments, the treatment with inert gas comprises use of a vacuum to remove the existing air and gases in the reaction chamber and replace with inert gas.

In some aspects, the process further comprises a step of sealing the reaction chamber. In some aspects, the sealing of the reaction chamber occurs immediately after the treatment with inert gas, or within a time period suitable to maintain an inert atmosphere in the reaction chamber. The sealing of the reaction chamber may be accomplished by any means sufficient to maintain an inert atmosphere. In some aspects, the reaction chamber comprises a glass vessel, and the sealing is accomplished by affixing to the vessel a lid or other covering that is sufficient to maintain the inert atmosphere. In some embodiments, the reaction comprises a laboratory grade borosilicate glass vessel, and the sealing is achieved with a screw-top lid, such as a metal lid, and the lid comprising a seal, such as a silicone seal.

In some aspects, after the sealing of the reaction chamber and before the initiating of the decarboxylation reaction, the sealed reaction vessel may be stored. In some embodiments, the sealed vessel may be stored at a temperature of about $-40°$ C. to about $-20°$ C. until a later time.

In some aspects, the process further comprises a step of initiating a decarboxylation reaction of the *cannabis* material in the sealed reaction chamber. In some aspects, the decarboxylation reaction occurs at a temperature and for a time period sufficient to allow for decarboxylation of one or more of the following compounds: tetrahydrocannabinolic acid (THCA), cannabidiolic acid (CBDA), and cannabigerolic acid (CBGA). In some embodiments, the decarboxylation reaction occurs at a temperature and for a time period sufficient to decarboxylate about 100%, or more than about 90%, or more than about 95%, or more than about 98%, by weight, of the THCA, CBDA, and CBGA. In some embodiments, the decarboxylation reaction occurs at a temperature and for a time period such that no, or substantially no, or no detectable amount of THCA, CBDA, and CBGA remain. In some aspects, the decarboxylation reaction occurs at a temperature of about $70°$ C. to about $150°$ C., or about $80°$ C. to about $140°$ C., or about $90°$ C. to about $130°$ C., or about $100°$ C. to about $130°$ C., or about $110°$ C. to about $125°$ C., or about $115°$ C. to about $120°$ C. In some aspects, the decarboxylation reaction may occur for a time period of about 0.5 hour to about 10 hours, or about 1 hour to about 8 hours, or about 1.5 hours to about 5 hours, or about 2 hours to about 3 hours. In some aspects, the decarboxylation reaction of the *cannabis* material occurs in a sealed reaction chamber and the reaction chamber is not unsealed during the decarboxylation reaction.

In some aspects, after the decarboxylation reaction, the process further comprises a step of condensing within the sealed reaction chamber. In some aspects, the condensing occurs at a temperature and for a time period sufficient to condense vapors. In some aspects the condensing occurs at a temperature of about −20° C. to about 40° C., or about −10° C. to about 30° C., or about 0° C. to about 20° C., or about 5° C. to about 15° C., or about 10° C. In some aspects, the condensing occurs for a time period of about 0.5 to 5 hours. In some aspects, the condensing step occurs in a sealed reaction chamber and the reaction chamber is not unsealed during the condensing step.

After the condensing step is completed, a decarboxylated cannabis composition is present in the reaction vessel, and the decarboxylated cannabis composition is retained within the sealed reaction chamber. The decarboxylated cannabis composition may be used immediately or stored until it is ready to be used. Optionally, the decarboxylated cannabis composition may be stored at a temperature of about −60° C. to about 0° C., or about −50° C. to about −10° C., or about −40° C. to about −20° C., for a period of time until ready for use. In some aspects, the decarboxylated cannabis composition may be stored in a sealed container. In some aspects, after the decarboxylated cannabis composition is retained within the sealed reaction chamber, the reaction chamber remains sealed until it is ready to be used, and the sealed reaction chamber containing the decarboxylated cannabis composition is stored.

When the decarboxylated cannabis composition is ready to be used, it may be heated to an appropriate temperature before use. This heating may occur after the decarboxylated cannabis composition is retained in the reaction chamber after the condensing step, or if it is stored for later use, the heating may occur after the storage and when the decarboxylated cannabis composition is ready to be used. In some aspects, the reaction chamber containing the decarboxylated cannabis composition may be heated to a temperature of about 50° C. to about 80° C., or about 65° C. to about 75° C. or about 70° C. In other aspects, the reaction chamber containing the decarboxylated cannabis composition may be heated to a temperature of about 50° C., about 55° C., about 60° C., or about 65° C. In some aspects, the decarboxylated cannabis composition is heated by placing the reaction chamber containing the decarboxylated cannabis composition in a water bath. In some aspects, the heating of the decarboxylated cannabis composition does not involve the use of coils in a reaction chamber. In some aspects, the decarboxylated cannabis composition remains in the sealed reaction chamber during the heating process, and the sealed reaction chamber is unsealed when brought to the appropriate temperature and/or is ready for use. In some aspects, the heating occurs after the sealed reaction chamber is unsealed, and the unsealed reaction chamber comprising the decarboxylated cannabis composition is placed in a water bath.

In some aspects, after the initial sealing of the reaction chamber, the reaction chamber remains sealed until the decarboxylated cannabis composition is retained and ready to be used. In some aspects, after the cannabis material is added to the reaction chamber and the reaction chamber is treated with inert gas, the reaction chamber is sealed, and the reaction chamber remains sealed during the decarboxylation reaction, the condensing step, and the formation of the decarboxylated cannabis composition, and the reaction vessel is unsealed only after the decarboxylated cannabis composition is formed and retained in the reaction vessel. In some aspects, no or substantially no substances (such as solvents or other additives) are added to the reaction chamber after treatment of the reaction chamber with inert gas, after the sealing of the reaction chamber, and/or after the initiating of the decarboxylation process. Solvents include, but are not limited to substances such as ethanol, isopropyl alcohol, n-propyl alcohol, methanol, butane, isobutane, propane, and carbon dioxide. Additives include any compound that is not present in the cannabis material, including but not limited to solvents, catalysts, reagents, surfactants, humectants, preservatives, antioxidants, flavoring agents, colorants, emulsifiers, stabilizers, thickeners, viscosity regulating agents, vitamins, minerals, and other excipients.

In some aspects, the reaction chamber is sealed after treatment with inert gas, the reaction chamber remains sealed until after the decarboxylation cannabis composition is formed and retained in the reaction chamber, and nothing (for example, no by-product) is removed from the reaction chamber prior to the unsealing of the sealed reaction chamber. The term "by-product" refers to secondary products derived from a chemical process, including by-products from the decarboxylation process. Examples of by-products include, but are not limited to carbon dioxide ($CO_2$). In some aspects, by-product may be released from the sealed reaction chamber once the reaction chamber is unsealed.

In some aspects, the decarboxylated cannabis composition comprises no or substantially no tetrahydrocannabinolic acid (THCA), cannabidiolic acid (CBDA), or cannabigerolic acid (CBGA). In some aspects, the decarboxylated cannabis composition comprises no or substantially no oxidation products, including but not limited to cannabinol (CBN). In some aspects, no or substantially no solvents or other additives are added to the decarboxylated cannabis composition and the decarboxylated cannabis composition comprise no or substantially no solvents or other additives. The term "no or substantially no" may refer to non-detectable amounts, or less than about 0.4%, or less than about 0.3%, or less than about 0.2%, or less than about 0.1%, or less than about 0.05%, or less than about 0.025%, or less than about 0.01%, or about 0%, by weight. The term "no or substantially no" may also refer to amounts insufficient to react with any other components.

In some aspects, the decarboxylated cannabis composition comprises one or more cannabinoids including but not limited to cannabidiol (CBD), cannabigerol (CBG), cannabidivarin (CBDV), cannabichromene (CBC), and tetrahydrocannabivarin (THCV), tetrahydrocannabinol (THC), delta-9 tetrahydrocannabinol, and delta-8 tetrahydrocannabinol. In some aspects, the decarboxylated cannabis composition comprises about 25% to about 95%, or about 25% to about 90%, or about 50% to about 90%, or about 60% to about 90%, or about 65% to about 90%, or about 70% to about 90%, or about 75% to about 90%, or about 80% to about 90%, by weight (wt. %) of one or more cannabinoids. These amounts may refer to the total amount of all cannabinoids, the total amount of one or more cannabinoids, or the total amount of one cannabinoid. In some aspects, these amounts refer to the amount of tetrahydrocannabinol (THC). In some aspects, the decarboxylated cannabis composition further comprises one or more terpenes. Terpenes include but are not limited to myrcene, caryophyllene, limonene, linalool, alpha-pinene, beta-pinene, humulene, terpinolene, alpha-bisabolol, eucalyptol, geraniol, terpineol, farnesene, borneol, ocimene, nerolidol, guaiol, valencene, delta-3 carene, phytol, sabinene, phellandrene, fenchol, menthol, terpinene, isoborneol, cymene, octanol, isopulegol, cedrene, camphene, geranyl acetate, bergamotene, camphor, and pulegon. In some aspects, the decarboxylated cannabis composition comprises about up to about 15%, or up to about 10%, or about 0% to about 10%, or about 0.1% to about 10%, or about 0.5% to about 8%, or about 0.75% to about 5%, or about 1% to about 4.5%, or about 2% to about 4.5%, or about 2.5% to about 4.5%, or about 5%, by weight (wt. %) of one or more terpenes. These amounts may refer to the total amount of all terpenes, the total amount of one or more terpenes, or the total amount of one terpene.

The present disclosure also relates to a composition comprising decarboxylated rosin, wherein the composition comprises no or substantially no additives and no or substantially no tetrahydrocannabinolic acid (THCA), cannabidiolic acid (CBDA), or cannabigerolic acid (CBGA). In some aspects, the decarboxylated rosin is obtained from a *cannabis* material comprising live rosin. In some aspects, the decarboxylated rosin comprises the cannabinoids and terpenes that were present in the rosin prior to decarboxylation. In some aspects, the decarboxylated rosin comprises the cannabinoids and terpenes in ratio amounts similar to those found prior to decarboxylation.

In some aspects, the decarboxylated *cannabis* composition comprises: total cannabinoids in an amount of 70 to 90%, tetrahydrocannabinol (THC) in an amount of 65 to 85%, tetrahydrocannabivarin (THCV) in an amount of 0 to 0.5%, cannabinol (CBN) in an amount of 0 to 0.4%, cannabigerol (CBG) in an amount of 1 to 4%, cannabichromene (CBC) in an amount of 1 to 2.5%, tetrahydrocannabinolic acid (THCA) in an amount of 0% (or not detectable amounts), cannabidiolic acid (CBDA) in an amount of 0% (or not detectable amounts), cannabigerolic acid (CBGA) in an amount of 0% (or not detectable amounts), and terpenes in a total amount of 2.5 to 10% (all wt. %).

In other aspects, any of the decarboxylated products described herein have more terpenes and cannabidiol preserved, and less oxidation of tetrahydrocannabinol to cannabinol, compared to a decarboxylated product produced by a traditional decarboxylation process (e.g., vacuum ovens, open vessels in traditional ovens).

In some aspects, the decarboxylated *cannabis* composition has a viscosity at 23° C., of less than about 10,000 cps, or less than about 5,000 cps, or less than about 2,000 cps, or less than about 1000 cps, or less than about 500 cps, or less than about 250 cps, or less than 100 cps, or less than about 50 cps.

In some aspects, after the reaction chamber is unsealed, the process further comprises filling a syringe or pipette, or any tool used to transport a volume of liquid, with an amount of decarboxylated *cannabis* composition. In some aspects, the transfer of the decarboxylated *cannabis* composition to the syringe, pipette, or other tool occurs immediately or shortly after the unsealing of the reaction chamber. In some aspects, the syringe, pipette, or other tool is heated to a temperature of about 55° C. to about 75° C., or about 60° C. to about 70° C., or about 65° C. prior to filling with the decarboxylated *cannabis* composition. In some aspects, the filled syringe, pipette, or other tool is maintained at a temperature of about 55° C. to about 75° C., or about 60° C. to about or about 65° C., until the contents of the syringe, pipette, or other tool are released. In some aspects, the syringe or pipette is made from glass, porcelain, or steel, or any material that will not react with the contents. In some aspects the syringe, pipette, or other tool is a borosilicate glass syringe or a borosilicate glass pipette.

In some aspects, the contents of the filled syringe, pipette, or other tool are transferred to a container for storage at a temperature of about −60° C. to about 0° C., or about −50° C. to about −10° C., or about −40° C. to about −20° C., for a period of time until ready for use. In some aspects, the contents of the filled syringe, pipette, or other tool are transferred to a vaporizer or a vaporizer cartridge. In some aspects, the temperature of the decarboxylated *cannabis* composition is maintained within a certain temperature range until it is ready to be used. For example, the temperature of the decarboxylated *cannabis* composition may be maintained within a temperature range of ±about 10° C., or about 8° C., or about 7° C., or about 6° C., or about 5° C., or about 4° C., or about 3° C., or about 2° C., or about 1° C.

In some aspects, the decarboxylated *cannabis* composition is a vaporizable composition, or a composition that is capable of being vaporized. In some aspects, the decarboxylated *cannabis* composition may be placed in a vaporizer or a vaporizer cartridge. The present disclosure also relates to a vaporizer or a vaporizer cartridge comprising the decarboxylated *cannabis* composition. The vaporizer or vaporizer cartridge may comprise a reservoir or chamber to hold the decarboxylated *cannabis* composition, and optionally an atomizer, a heating element, and a power source, such as a battery. In some aspects, the heating element may be ceramic heating elements. In some aspects, the battery may be charged, for example, via a USB port or micro USB port. In some aspects, the vaporizer or vaporizer cartridge may also comprise an indicator such as an LED light. In some aspects, the decarboxylated *cannabis* composition may be used to fill the storage chamber or cartridge of a single-use vaporizer comprising a 0.25 g to 2 g cartridge/chamber, a heating element and/or atomizer, including but not limited to a ceramic heating element and/or atomizer, and optionally a 280 mah to 350 mah battery in a metal casing.

In some aspects, the present disclosure related to a single-use, all-in-one vaporizer comprises a 0.5 gram chamber filled with the 0.3 g decarboxylated *cannabis*, a 260 mah battery that operates at 3.5V, a micro USB port for charging, a LED light that glows with operation. The single-use, all-in-one vaporizer is wrapped one an anodized aluminum casing. The decarboxylated *cannabis* composition comprises: total cannabinoids in an amount of 70 to 90%, tetrahydrocannabinol (THC) in an amount of 65 to 85%, tetrahydrocannabivarin (THCV) in an amount of 0 to 0.5%, cannabinol (CBN) in an amount of 0 to 0.4%, cannabigerol (CBG) in an amount of 1 to 4%, cannabichromene (CBC) in an amount of 1 to 2.5%, tetrahydrocannabinolic acid (THCA) in an amount of 0% (or not detectable amounts), cannabidiolic acid (CBDA) in an amount of 0% (or not detectable amounts), cannabigerolic acid (CBGA) in an amount of 0% (or not detectable amounts), and terpenes in a total amount of 2.5 to 10%.

The goal of decarboxylating a *cannabis* extract is to activate THCa to delta-9 THC (D9-THC), the biologically active version of the molecule that is liquid rather than crystalline at room temperature. There are byproducts of any decarboxylation method that can be compared once all the THCA has been converted. The methods described herein and exemplified below are an improvement over current processes and provide desired products.

EXAMPLES

Example 1

The following is an exemplary process of preparing a decarboxylated *cannabis* composition:

1. A laboratory-grade borosilicate glass jar having a metal screw-top lined with a plastisol or silicone-lined, heatproof seal, is cleaned with pure ethanol, followed by a complete rinse with distilled or filtered water and dried.

2. Rosin or resin is placed in the jar.

3. An inert gas (nitrogen or argon) is used to purge the air from the jar and to create an inert atmosphere. Using a handheld nozzle attached to a gas tank, with jar top unscrewed and slightly opened, all of the air in the jar is displaced with a blast of inert gas. The lid is then screwed onto the jar to create a sealed jar. The inert gas blankets the rosin or resin in the jar, resulting in a low oxygen, low reactivity environment.

4. The sealed jar is heated to a temperature of about 118° C. for 2 to 3 hours in a precision oven or decarboxylator, and decarboxylation of the rosin and resin occurs.

5. The jar containing decarboxylated rosin or resin remains sealed and is then rapidly cooled, immediately after the decarboxylation, at a temperature of about 10° C. to allow for condensation of any volatized compounds including volatized terpenes.

6. The resulting decarboxylated rosin or resin composition then may be used, for example, in a vaporizer or vaporizer cartridge. The decarboxylated rosin or resin composition may be transferred to a borosilicate glass syringe that has been previously heated to a temperature of 60° C. to 70° C., and the temperature of the glass syringe is maintained at this temperature until the contents are transferred.

7. If the resulting decarboxylated rosin or resin composition is not to be used immediately, the composition may be kept frozen and stored. When ready to be used, the frozen decarboxylated rosin or resin composition may be placed in a water bath heated to a temperature of about 72° C. The use of a direct heating element or oil bath are avoided, to prevent burning or scalding of the composition and to minimize high temperatures that may oxidize or evaporate terpenes.

Example 2

The following represents an exemplary decarboxylated *cannabis* composition, obtained from live rosin starting material:

| Component | Amount (wt. %) |
|---|---|
| Total cannabinoids | 70 to 90% |
| Tetrahydrocannabinol (THC) | 65 to 85% |
| Tetrahydrocannabivarin (THCV) | 0 to 0.5% |
| Cannabinol (CBN) | 0 to 0.4% |
| Cannabigerol (CBG) | 1 to 4% |
| Cannabichromene (CBC) | 1 to 2.5% |
| Tetrahydrocannabinolic acid (THCA) | 0%* |
| Cannabidiolic acid (CBDA) | 0%* |
| Cannabigerolic acid (CBGA) | 0%* |
| Total terpenes | 2.5 to 10% |

*Not detected

Example 3

The following represents comparative data between (1) Raw rosin made from fresh frozen flower (KM-R); (2) Rosin decarboxylated using a traditional open vessel in a normal air-filled oven (KM-0); and (3) Rosin decarboxylated using the process described in Example 1 (KM-M).

| mg/g | Raw Rosin (KM-R) | Traditional Open Decarb (KM-O) | Example 1 Process (KM-M) | KM-M vs. KM-O (%) or KM-O vs. KM-M (%) | |
|---|---|---|---|---|---|
| THCA | 814.75 | 0.00 | 0.00 | | |
| D9-THC | 59.28 | 828.03 | 810.45 | | Higher apparent THC% in open vessel due to loss of terpenes |
| THCV | 0.00 | 4.67 | 4.60 | | |
| CBDA | 1.46 | 0.00 | 0.00 | | |
| CBD | 5.05 | 1.80 | 2.23 | 124% | 24% more CBD preserved |
| CBN | 0.00 | 0.67 | 0.58 | 115% | 15% less THC -> CBN oxidation |
| CBGA | 40.25 | 0.00 | 0.00 | | |
| CBG | 3.30 | 43.10 | 42.69 | | |
| CBC | 0.00 | 11.20 | 10.64 | | |
| Total THC | 773.82 | 828.03 | 810.45 | | |
| Total CBD | 6.33 | 1.80 | 2.23 | | |
| Total | 818.77 | 889.48 | 871.19 | | |
| Total Terpenes % | 4.31 | 2.19 | 3.94 | 180% | 80% more terpenes preserved |
| Terpene LOSS compared to RAW | | 49.152% | 8.508% | | |

Compared to the traditional method of decarboxylation using vacuum ovens and/or open vessels in traditional ovens, the inventive process described herein resulted in:

80% more terpenes preserved;

24% more CBD preserved; and

15% less oxidation of THC to CBN.

Moreover, the inventive process resulted in a complete decarboxylation of all THCA and CBDA.

The results show that the inventive process provides better retention, preservation and activation of the original flavors and cannabinoids, while creating a room-temperature liquid and more stable version of rosin that can be much more easily vaporized, with an extended shelf life.

Terpenes are the flavors of the extract. In raw form, they have the original flavors of the plant on the day of harvest. Any oxidation changes the flavor profile. The inventive process described herein prevents the vast majority of terpene oxidation and evaporation—maximally preserving the original flavor profile and preventing "off notes" that can ruin the entire extract flavor for the rosin consumer. Preserving the terpenes also preserves the "entourage effect"— the natural combination of THC, other cannabinoids and terpenes that creates a *cannabis* strain's unique high. By preserving the original terpenes in the rosin, the inventive process described herein maintains the fidelity of the entourage effect of the activated liquid rosin to the original raw rosin.

CBD: Along with the primary goal of fully decarboxylating THCA to THC, CBDA also decarboxylates to CBD in this process, but CBD can also break down further under heat in an open or air-filled container. The inventive process described herein provides a 24% better yield of preserving the existing CBD, which is one of the most desirable molecules in the extract.

CBN: CBN levels are used in raw flower to gauge the age of the product, as THC breaks down to CBN over time.

Open vessel decarboxylation creates 15% more CBN than the process of the present invention. While CBN only represents THC/CBD oxidation, the metric can be used to give an overall sense of the lower oxidation of molecules of all types with the novel process of the inventive process described herein. CBN itself when present in the extract in larger amounts results in a tired, groggy feeling for the consumer so it is ideally kept at the lowest possible levels.

Overall, the data shows that the inventive rosin activation and liquification process described herein better preserves the flavors and biologically active and sought-after components in the *cannabis* extract compared to a traditional decarboxylation process. When used in a vaporizer, the decarboxylated product described herein results in a better flavor and effect for the consumer, and a cleaner, purer product without additives or solvents, and thus a markedly better product overall.

Example 4

A single-use, all-in-one vaporizer comprises a 0.5 gram chamber filled with the 0.3 g decarboxylated *cannabis* composition of Example 2 or 3, a 260 mAh battery that operates at 3.5V, a micro USB port for charging, a LED light that glows with operation. The single-use, all-in-one vaporizer is wrapped one an anodized aluminum casing.

What is claimed:

1. A method for preparing a decarboxylated *cannabis* composition, comprising:
   (a) adding *cannabis* material to a reaction chamber,
   (b) treating the reaction chamber with inert gas,
   (c) sealing the reaction chamber,
   (d) initiating a decarboxylation reaction of the *cannabis* material at about 70° C. to about 150° C., for about 0.5 hour to about 10 hours in the sealed reaction chamber,
   (e) condensing within the sealed reaction chamber at about 0° C. to about 20° C.,
   (f) retaining a decarboxylated *cannabis* composition within the sealed reaction chamber,
   (g) optionally, storing the sealed reaction chamber comprising the decarboxylated *cannabis* composition at a temperature of about −40° C. to about −20° C., and
   (h) unsealing the sealed reaction chamber to form an unsealed reaction chamber comprising the decarboxylated *cannabis* composition,
   wherein no or substantially no solvent is added to the reaction chamber, and
   wherein no by-products are removed from the reaction chamber prior to the unsealing of the sealed reaction chamber.

2. The method of claim 1, wherein after step (h), the unsealed reaction chamber is placed in a water bath and heated to a temperature of about 50° C. to about 80° C. or 65° C. to about 75° C.

3. The method of claim 1, further comprising filling a syringe or pipette with an amount of decarboxylated *cannabis* composition,
   wherein the syringe or pipette is heated to a temperature of about 55° C. to about 75° C. or about 60° C. to about 70° C. prior to filling, and
   wherein the filled syringed or pipette is maintained at a temperature of about 55° C. to about 75° C. or about 60° C. to about 70° C.

4. The method of claim 3, wherein the syringe or pipette is a borosilicate glass syringe or borosilicate glass pipette.

5. The method of any of claim 3, further comprising transferring the contents of the filled syringe or pipette into a vaporizer or vaporizer cartridge.

6. The method of claim 1, wherein after step (c), the reaction chamber remains sealed until step (h).

7. The method of claim 1, wherein the reaction chamber does not contain a filter or coils.

8. The method of claim 1, further comprising placing an amount of the decarboxylated *cannabis* composition into a vaporizer or a vaporizer cartridge.

9. The method of claim 8, wherein no solvents or additives are added to the decarboxylated *cannabis* composition prior to placing in a vaporizer or a vaporizer cartridge.

10. The method of claim 9, wherein no flavoring agents are added to the decarboxylated *cannabis* composition prior to placing in a vaporizer or a vaporizer cartridge.

11. The method of claim 1, wherein the *cannabis* material comprises a *cannabis* extract, a *cannabis* concentrate, dried or live plant matter, or a mixture thereof.

12. The method of claim 1, wherein the *cannabis* material comprises no or substantially no solvent.

13. The method of claim 1, wherein the inert gas comprises nitrogen or argon gas.

14. The method of claim 1, wherein the reaction chamber is a glass vessel.

15. The method of claim 1, wherein step (d) occurs at about 90° C. to about 130° C. or about 110° C. to about 125° C.

16. The method of claim 1, wherein step (d) occurs for about 1 to about 5 hours or about 2 to about 3 hours.

17. The method of claim 1, wherein the decarboxylated *cannabis* composition comprises no additives and substantially no tetrahydrocannabinolic acid (THCA), cannabidiolic acid (CBDA), or cannabigerolic acid (CBGA).

18. The method of claim 1, further comprising (g) storing the sealed reaction chamber comprising the decarboxylated cannabis composition at a temperature of about −40° C. to about −20° C.

19. The method of claim 18, wherein after step (g), the sealed reaction chamber is placed in a water bath and heated to a temperature of about 50° C. to about 80° C. or about 65° C. to about 75° C.

20. The method of claim 3, wherein the syringe or pipette is made from glass, porcelain, or steel.

* * * * *